(12) United States Patent
Cox et al.

(10) Patent No.: US 8,568,405 B2
(45) Date of Patent: Oct. 29, 2013

(54) ELECTROSURGICAL WAND AND RELATED METHOD AND SYSTEM

(75) Inventors: David A. Cox, Austin, TX (US); Johnson E. Goode, Austin, TX (US); Philip M. Tetzlaff, Austin, TX (US); Jean Woloszko, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 593 days.

(21) Appl. No.: 12/905,438

(22) Filed: Oct. 15, 2010

(65) Prior Publication Data

US 2012/0095454 A1    Apr. 19, 2012

(51) Int. Cl.
*A61B 18/14*    (2006.01)

(52) U.S. Cl.
USPC ............................................... 606/41

(58) Field of Classification Search
USPC ................................. 606/27, 34, 41
See application file for complete search history.

(56) References Cited

U.S. PATENT DOCUMENTS

| | | | |
|---|---|---|---|
| 2,050,904 A | 4/1936 | Trice | 219/31 |
| 2,056,377 A | 10/1939 | Wappler | 125/303 |
| 3,633,425 A | 1/1972 | Sanford | 73/356 |
| 3,707,149 A | 12/1972 | Hao et al. | 128/303.14 |
| 3,718,617 A | 2/1973 | Royal | 260/30.4 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,963,030 A | 6/1976 | Newton | 606/40 |
| 3,964,487 A | 6/1976 | Judson | 606/39 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |

(Continued)

FOREIGN PATENT DOCUMENTS

| | | | | |
|---|---|---|---|---|
| DE | 3119735 | | 1/1983 | A61B 17/39 |
| DE | 3930451 A1 | | 3/1991 | A61B 17/39 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Michael Peffley
*Assistant Examiner* — Daniel Fowler
(74) *Attorney, Agent, or Firm* — Matthew Scheele; Brian E. Szymczak

(57) ABSTRACT

Electrosurgical wand. At least some of the illustrative embodiment are electrosurgical wands including: an elongate housing that defines a handle end and a distal end; an aspiration aperture on the distal end of the elongate housing the aspiration aperture fluidly coupled to a first fluid conduit, the first fluid conduit within the elongate housing; a discharge aperture on the distal end of the elongate housing, the discharge aperture fluidly coupled to a second fluid conduit, and the second fluid conduit within the elongate housing; a first active electrode of conductive material on the distal end of the elongate housing, the first active electrode between the discharge aperture and the aspiration aperture; and a conductive plate that abuts the discharge aperture, at least a portion of the conductive plate disposed over the discharge aperture.

26 Claims, 9 Drawing Sheets

(56) References Cited

U.S. PATENT DOCUMENTS

| | | | |
|---|---|---|---|
| 4,074,718 A | 2/1978 | Morrison, Jr. | 128/303 |
| 4,092,986 A | 6/1978 | Schneiderman | 128/303 |
| 4,114,623 A | 9/1978 | Meinke et al. | 606/39 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 600/505 |
| 4,248,231 A | 2/1981 | Herczog et al. | 128/303 |
| 4,301,801 A | 11/1981 | Schneiderman | 606/38 |
| 4,326,529 A | 4/1982 | Doss et al. | 128/303 |
| 4,346,715 A | 8/1982 | Gammell | 607/99 |
| 4,378,801 A | 4/1983 | Oosten | 606/37 |
| 4,381,007 A | 4/1983 | Doss | 128/303 |
| 4,418,692 A | 12/1983 | Guay | 606/27 |
| 4,474,179 A | 10/1984 | Koch | 606/40 |
| 4,476,862 A | 10/1984 | Pao | 128/303 |
| 4,509,532 A | 4/1985 | DeVries | 128/736 |
| 4,520,818 A | 6/1985 | Mickiewicz | 606/40 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,572,206 A | 2/1986 | Geddes et al. | 600/505 |
| 4,580,557 A | 4/1986 | Hertzmann | 606/12 |
| 4,587,975 A | 5/1986 | Salo et al. | 600/506 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,750,902 A | 6/1988 | Wuchinich et al. | 604/22 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,860,752 A | 8/1989 | Turner | 607/102 |
| 4,898,169 A | 2/1990 | Norman et al. | 606/42 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 607/105 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,026,387 A | 6/1991 | Thomas | 606/169 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,080,660 A | 1/1992 | Buelna | 606/45 |
| 5,083,565 A | 1/1992 | Parins et al. | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 606/505 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,174,304 A | 12/1992 | Latina et al. | 607/141 |
| 5,178,620 A | 1/1993 | Eggers et al. | 606/41 |
| 5,183,338 A | 2/1993 | Wickersheim et al. | 374/131 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,249,585 A | 10/1993 | Turner et al. | 607/99 |
| 5,255,980 A | 10/1993 | Thomas et al. | 374/161 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,282,799 A | 2/1994 | Rydell | 606/48 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,324,254 A | 6/1994 | Phillips | 604/21 |
| 5,330,470 A | 7/1994 | Hagen | 606/42 |
| 5,334,140 A | 8/1994 | Philips | 604/35 |
| 5,334,183 A | 8/1994 | Wuchinich | 606/46 |
| 5,334,193 A | 8/1994 | Nardella | 606/41 |
| 5,336,220 A | 8/1994 | Ryan et al. | 604/22 |
| 5,336,443 A | 8/1994 | Odashima | 252/511 |
| 5,342,357 A | 8/1994 | Nardella | 606/40 |
| 5,348,554 A | 9/1994 | Imran et al. | 606/41 |
| 5,363,324 A | 11/1994 | Hashimoto et al. | 365/156 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,472,443 A | 12/1995 | Cordis et al. | 606/48 |
| 5,486,161 A | 1/1996 | Lax et al. | 604/22 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,730 A | 4/1996 | Edwards | 606/41 |
| 5,507,743 A | 4/1996 | Edwards et al. | 606/41 |
| 5,514,130 A | 5/1996 | Baker | 606/41 |
| 5,540,683 A | 7/1996 | Ichikawa et al. | 606/40 |

(56) References Cited

U.S. PATENT DOCUMENTS

| | | | |
|---|---|---|---|
| 5,542,915 A | 8/1996 | Edwards et al. | 604/22 |
| 5,549,598 A | 8/1996 | O'Donnell, Jr. | 606/6 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |
| 5,588,960 A | 12/1996 | Edwards et al. | 604/20 |
| 5,599,350 A | 2/1997 | Schulze et al. | 606/51 |
| 5,609,151 A | 3/1997 | Mulier et al. | 128/642 |
| 5,633,578 A | 5/1997 | Eggers et al. | 323/301 |
| 5,634,921 A | 6/1997 | Hood et al. | 606/5 |
| 5,643,304 A | 7/1997 | Schechter et al. | 606/171 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,697,927 A | 12/1997 | Imran et al. | 606/41 |
| 5,700,262 A | 12/1997 | Acosta et al. | 606/48 |
| 5,715,817 A | 2/1998 | Stevens-Wright et al. | 600/373 |
| 5,722,975 A | 3/1998 | Edwards et al. | 606/41 |
| 5,725,524 A | 3/1998 | Mulier et al. | 606/41 |
| 5,749,869 A | 5/1998 | Lindenmeier et al. | 606/34 |
| 5,749,871 A | 5/1998 | Hood et al. | 606/50 |
| 5,749,914 A | 5/1998 | Janssen | 607/116 |
| 5,755,753 A | 5/1998 | Knowlton | 607/98 |
| 5,766,153 A | 6/1998 | Eggers et al. | 604/114 |
| 5,769,847 A | 6/1998 | Panescu et al. | 606/42 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,873,877 A | 2/1999 | McGaffigan | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 5,964,786 A | 10/1999 | Ochs et al. | 607/5 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,068,628 A | 5/2000 | Fanton et al. | 606/41 |
| 6,074,386 A | 6/2000 | Goble et al. | 606/34 |
| 6,090,106 A | 7/2000 | Goble et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |
| 6,159,194 A | 12/2000 | Eggers et al. | 604/500 |
| 6,159,208 A | 12/2000 | Hovda et al. | 606/41 |
| 6,162,217 A | 12/2000 | Kannenberg et al. | 606/34 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,021 B1 | 3/2001 | Panescu et al. | 606/31 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 606/32 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 606/41 |
| 6,254,600 B1 | 7/2001 | Willink et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 604/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,322,549 B1 | 11/2001 | Eggers et al. | 604/500 |
| 6,346,104 B2 | 2/2002 | Daly et al. | 606/34 |
| 6,346,107 B1 | 2/2002 | Cucin | 606/49 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |
| 6,409,722 B1 | 6/2002 | Hoey et al. | 606/34 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,432,103 B1 | 8/2002 | Ellsberry et al. | 606/41 |
| 6,440,129 B1 | 8/2002 | Simpson | 606/42 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,514,250 B1 | 2/2003 | Jahns et al. | 606/41 |
| 6,517,498 B1 | 2/2003 | Burbank et al. | 600/564 |
| 6,530,922 B2 | 3/2003 | Cosman | 606/34 |
| 6,558,382 B2 | 5/2003 | Jahns et al. | 606/41 |
| 6,565,560 B1 | 5/2003 | Goble et al. | 606/41 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,635,034 B1 | 10/2003 | Cosmescu | 604/289 |
| 6,656,177 B2 | 12/2003 | Truckai et al. | 606/51 |
| 6,730,080 B2 | 5/2004 | Harano et al. | 606/38 |
| 6,749,604 B1 | 6/2004 | Eggers et al. | 606/41 |
| 6,749,608 B2 | 6/2004 | Garito et al. | 606/45 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |

(56) References Cited

U.S. PATENT DOCUMENTS

| | | | |
|---|---|---|---|
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,866,671 B2 | 3/2005 | Tierney et al. | 606/130 |
| 6,878,149 B2 | 4/2005 | Gatto | 606/46 |
| 6,890,307 B2 | 5/2005 | Kokate et al. | 600/549 |
| 6,892,086 B2 | 5/2005 | Russell | 600/372 |
| 6,911,027 B1 | 6/2005 | Edwards et al. | 606/40 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,770 B2 | 1/2006 | Hood | 606/41 |
| 6,991,631 B2 | 1/2006 | Woloszko et al. | 606/41 |
| 7,001,382 B2 | 2/2006 | Gallo | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,094,231 B1 | 8/2006 | Ellman et al. | 606/37 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,247,155 B2 | 7/2007 | Hoey et al. | 606/34 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,276,063 B2 | 10/2007 | Davison et al. | 606/45 |
| 7,278,994 B2 | 10/2007 | Goble | 606/41 |
| 7,282,048 B2 | 10/2007 | Goble et al. | 606/34 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| 7,335,199 B2 | 2/2008 | Goble et al. | 606/41 |
| RE40,156 E | 3/2008 | Sharps et al. | 606/32 |
| 7,344,532 B2 | 3/2008 | Goble et al. | 606/34 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/41 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,572,251 B1 | 8/2009 | Davison et al. | 604/500 |
| 7,632,267 B2 | 12/2009 | Dahla | 606/41 |
| 7,678,069 B1 | 3/2010 | Baker et al. | 604/22 |
| 7,691,101 B2 | 4/2010 | Davison et al. | 606/41 |
| 7,704,249 B2 | 4/2010 | Woloszko et al. | 606/48 |
| 7,708,733 B2 | 5/2010 | Sanders et al. | 606/41 |
| 2002/0029036 A1 | 3/2002 | Goble et al. | 606/38 |
| 2002/0042612 A1 | 4/2002 | Hood et al. | 606/50 |
| 2002/0151882 A1 | 10/2002 | Marko et al. | 606/28 |
| 2002/0183739 A1 | 12/2002 | Long | 606/41 |
| 2003/0013986 A1 | 1/2003 | Saadat | 600/549 |
| 2003/0014045 A1 | 1/2003 | Russell | 606/41 |
| 2003/0014047 A1 | 1/2003 | Woloszko et al. | 606/41 |
| 2003/0088245 A1 | 5/2003 | Woloszko et al. | 606/41 |
| 2003/0130655 A1 | 7/2003 | Woloszko et al. | 606/45 |
| 2003/0158545 A1 | 8/2003 | Hovda et al. | 606/32 |
| 2003/0171743 A1 | 9/2003 | Tasto et al. | 606/32 |
| 2003/0181903 A1 | 9/2003 | Hood et al. | 606/49 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 606/41 |
| 2003/0216732 A1 | 11/2003 | Truckai et al. | 606/49 |
| 2004/0030330 A1 | 2/2004 | Brassell et al. | 606/41 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Hovda et al. | 606/41 |
| 2005/0033278 A1 | 2/2005 | McClurken et al. | 606/34 |
| 2005/0261754 A1 | 11/2005 | Woloszko et al. | 606/32 |
| 2005/0273091 A1 | 12/2005 | Booth et al. | 607/99 |
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0208334 A1 | 9/2007 | Woloszko et al. | 606/41 |
| 2007/0208335 A1 | 9/2007 | Woloszko et al. | 606/41 |
| 2007/0282323 A1 | 12/2007 | Woloszko et al. | 606/41 |
| 2008/0004621 A1 | 1/2008 | Dahla et al. | 606/48 |
| 2008/0077128 A1 | 3/2008 | Woloszko et al. | 606/41 |
| 2008/0154255 A1 | 6/2008 | Panos et al. | 606/33 |
| 2008/0167645 A1 | 7/2008 | Woloszko | 606/40 |
| 2008/0234671 A1 | 9/2008 | Marion | 606/41 |
| 2008/0243116 A1 | 10/2008 | Anderson | 606/41 |
| 2008/0300590 A1 | 12/2008 | Horne et al. | 606/35 |
| 2009/0209956 A1 | 8/2009 | Marion | 606/34 |
| 2010/0152726 A1 | 6/2010 | Cadouri et al. | 606/41 |
| 2010/0228246 A1 | 9/2010 | Marion | 606/37 |

FOREIGN PATENT DOCUMENTS

| | | | |
|---|---|---|---|
| EP | 423757 | 3/1996 | A61B 17/39 |
| EP | 0703461 A2 | 3/1996 | G01B 27/02 |
| EP | 0740926 A2 | 11/1996 | A61B 17/39 |
| EP | 0754437 A2 | 1/1997 | A61B 17/39 |
| EP | 0694290 B1 | 11/2000 | A61B 18/04 |
| EP | 1334699 | 8/2003 | A61B 18/12 |
| EP | 1428480 | 6/2004 | A61B 18/12 |
| EP | 1707147 | 10/2006 | A61B 18/12 |
| FR | 2313949 | 1/1977 | A61N 3/02 |
| GB | 467502 | 6/1937 | |
| GB | 2160102 | 12/1985 | A61B 17/38 |
| GB | 2299216 | 9/1996 | H01F 30/12 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2333455 | 7/1999 | G01K 11/12 |
| GB | 2406793 | 4/2005 | A61B 18/00 |
| JP | 57-57802 | 4/1982 | A61B 1/00 |
| JP | 57-117843 | 7/1982 | A61B 17/39 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | |
| WO | 94/08654 | 4/1994 | A61M 37/00 |
| WO | 94/10921 | 5/1994 | A61B 18/00 |
| WO | 94/26228 | 11/1994 | A61B 18/14 |
| WO | 95/34259 | 12/1995 | A61F 5/48 |
| WO | 96/00040 | 1/1996 | A61B 18/00 |
| WO | 96/00042 | 1/1996 | A61B 17/39 |
| WO | 96/39086 | 12/1996 | A61B 18/12 |

(56) References Cited

FOREIGN PATENT DOCUMENTS

| | | | |
|---|---|---|---|
| WO | 97/00646 | 1/1997 | A61B 17/39 |
| WO | 97/00647 | 1/1997 | A61B 17/39 |
| WO | 97/18768 | 5/1997 | A61B 17/39 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/43971 | 11/1997 | A61B 17/39 |
| WO | 97/48345 | 12/1997 | A61B 17/39 |
| WO | 97/48346 | 12/1997 | A61B 17/39 |
| WO | 98/07468 | 2/1998 | A61N 1/40 |
| WO | 98/26724 | 6/1998 | A61B 17/36 |
| WO | 98/27879 | 7/1998 | A61B 17/36 |
| WO | 98/27880 | 7/1998 | A61B 17/39 |
| WO | 99/20213 | 4/1999 | A61F 7/12 |
| WO | 99/51155 | 10/1999 | A61B 17/36 |
| WO | 99/51158 | 10/1999 | A61B 17/39 |
| WO | 99/56648 | 11/1999 | A61B 17/39 |
| WO | 00/00098 | 1/2000 | A61B 17/36 |
| WO | 00/09053 | 2/2000 | A61F 7/12 |
| WO | 01/24720 | 4/2001 | A61B 18/18 |
| WO | 01/87154 | 5/2001 | A61B 5/05 |
| WO | 02/02255 | 1/2002 | A61B 17/20 |
| WO | 02/36028 | 5/2002 | A61B 18/12 |
| WO | 03/024305 | 3/2003 | |
| WO | 03/092477 | 11/2003 | |
| WO | 2004/026150 | 4/2004 | A61B 17/22 |
| WO | 2004/071278 | 8/2004 | |
| WO | 2005/125287 | 12/2005 | A61B 18/00 |
| WO | 2007/006000 | 1/2007 | A61B 18/14 |
| WO | 2007/056729 | 5/2007 | A61B 18/14 |

OTHER PUBLICATIONS

BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" Bio-Medical Engineering vol. 4, pp. 206-216, May 1969.
Elsasser, V.E. et al., "An Instrument for Transurethral Resection without Leakage of Current" Acta Medicotechnica vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" IEEE pp. 58-65 1975.
Kramolowsky et al. "The Urological App of Electorsurgery" J. of Urology vol. 146, pp. 669-674, 1991.
Kramolowsky et al. "Use of 5F Bipolar Electrosurgical Probe in Endoscopic Urological Procedures" J. of Urology vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.

Lu, et al., "Electrical Thermal Angioplasty: Catheter Design Features, in Vitro Tissue Ablation Studies and in Vitro Experimental Findings," Am J. Cardiol vol. 60, pp. 1117-1122, Nov. 1, 1987.
Malis, L., "Electrosurgery, Technical Note," J. Neursurg., vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" Cerebrovascular Surgery, vol. 1, pp. 245-260, 1985.
Malis, L., "New Trends in Microsurgery and Applied Technology," Advanced Technology in Neurosurgery, pp. 1-16, 1988.
Malis, L., "The Value of Irrigation During Bipolar Coagulation" See ARTC 21602, 1 pg, Apr. 9, 1993.
Nardella, P.C., SPIE 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" Gastroenterology vol. 74(3), pp. 527-534, 1978.
Protell et al., "Computer-Assisted Electrocoagulation: Bipolar v. Monopolar in the Treatment of Experimental Canine Gastric Ulcer Bleeding," Gastroenterology vol. 80, No. 3, pp. 451-455, 1981.
Ramsey et al., "A Comparison of Bipolar and Monopolar Diathermy Probes in Experimental Animals", Urological Research vol. 13, pp. 99-102, 1985.
Selikowitz et al., "Electric Current and Voltage Recordings on the Myocardium During Electrosurgical Procedures in Canines," Surgery, Gynecology & Obstetrics, vol. 164, pp. 219-224, Mar. 1987.
Shuman, "Bipolar Versus Monopolar Electrosurgery: Clinical Applications," Dentistry Today, vol. 20, No. 12, 7 pgs, Dec. 2001.
Slager et al. "Spark Erosion of Arteriosclerotic Plaques" Z. Kardiol. 76:Suppl. 6, pp. 67-71, 1987.
Slager et al. "Vaporization of Atheroscleroticc Plaques by Spark Erosion" JACC 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.

(56) References Cited

OTHER PUBLICATIONS

Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia Coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of Excherichia Coli and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for in Vivo Medical Treatment: Recent Developments and Perspectives", Plasma Sources Sci. Technol. 15, pp. S169-S180, Nov. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Buchelt, et al. "Excimer Laser Ablation of Fibrocartilage: An in Vitro and in Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.
European Examination Report for EP 02773432 4 pgs, Sep. 22, 2009.
European Examination Report for EP 05024974 4 pgs, Dec. 5, 2008.
European Examination Report for EP 04708664 7pgs, Sep. 7, 2009.
European Examination Report for EP 02749601.7 4pgs, Dec. 2, 2009.
European Examination Report 2 for EP 04708664 5pgs, May 3, 2010.
European Search Report for EP 02773432 3pgs, Dec. 19, 2008.
European Search Report for EP 04708664.0 5pgs, Apr. 6, 2009.
European Search Report for EP 98953859, 2 pgs, Jul. 2, 2001.
Suppl European Search Report for EP 98953859, 3 pgs, Oct. 18, 2001.
Extended European Search Report for EP09152846, 8pgs, Jan. 5, 2010.
European Search Report for EP 99945039.8, 3 pgs, Oct. 1, 2001.
European Search Report for EP 09152850, 2 pgs, Dec. 29, 2009.
PCT International Preliminary Examination Report for PCT/US02/19261, 3pgs, Mar. 25, 2003.
PCT International Search Report for PCT/US02/19261, 1 pg, Mailed Sep. 18, 2002.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT International Search Report for PCT/US98/22323, 1 pg, Mailed Mar. 3, 1999.
PCT International Search Report for PCT/US99/14685, 1 pg, Mailed Oct. 21, 1999.
PCT International Search Report for PCT/US99/18289, 1 pg, Mailed Dec. 7, 1999.
PCT Notification of International Preliminary Examination Report for PCT/US98/22323, 5 pgs, Mailed Nov. 28, 2000.
PCT Notification of International Preliminary Examination Report for PCT/US99/14685, 4 pgs, Mailed Feb. 20, 2001.
PCT Notification of International Preliminary Examination Report for PCT/US99/18289, 4 pgs, Mailed Jul. 7, 2000.
PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
PCT Notification of the International Search Report and Written Opinion for PCT/US07/69856, 7pgs, Mailed Jun. 5, 2008.
PCT Written Opinion of the International Searching Authority for PCT/US04/03614, 4 pgs, Mailed Sep. 14, 2004.
UK Search Report for GB0800129.9 2pgs, May 8, 2008.
UK Search Report for GB0805062.7 1 pg, Jul. 16, 2008.
UK Search Report for GB0900604.0 4 pgs, May 15, 2009.
Slager et al., "Electrical nerve and Muscle Stimulation by Radio Frequency Surgery: Role of Direct Current Loops Around the Active Electrode", IEEE Transactions on Biomedical engineering, vol. 40, No. 2, pp. 182-187, Feb. 1993.

US 8,568,405 B2

1

ELECTROSURGICAL WAND AND RELATED METHOD AND SYSTEM

CROSS-REFERENCE TO RELATED APPLICATIONS

None.

BACKGROUND

In the treatment of chronic wounds (e.g., diabetic foot ulcers) electrosurgical procedures may be used to promote healing. In particular, electrosurgical procedures may be used for debriding the wound, inducing blood flow to the wound, coagulating blood flow from the wound, removing necrotic tissue, and/or removing bacterial films which may form (the bacterial films sometimes referred to as "biofilm"). In many cases wounds are considered "dry" in the sense that there is insufficient conductive fluid present to support plasma creation for electrosurgical procedures. In such cases a conductive fluid (e.g., saline) is provided to help support plasma creation.

However, in providing a conductive fluid to a wound to help support plasma creation, the location of the wound and/or the orientation of the patient may adversely impact how the conductive fluid is distributed. For example, gravity may cause the conductive fluid to flow in such a way as to not fully "wet" one or more of the electrodes involved in the plasma creation, thus limiting or preventing plasma creation.

Any advance that better controls distribution of conductive fluid in and around the electrodes of an electrosurgical system would provide a competitive advantage.

BRIEF DESCRIPTION OF THE DRAWINGS

For a detailed description of exemplary embodiments, reference will now be made to the accompanying drawings in which.

2

Figure 12:
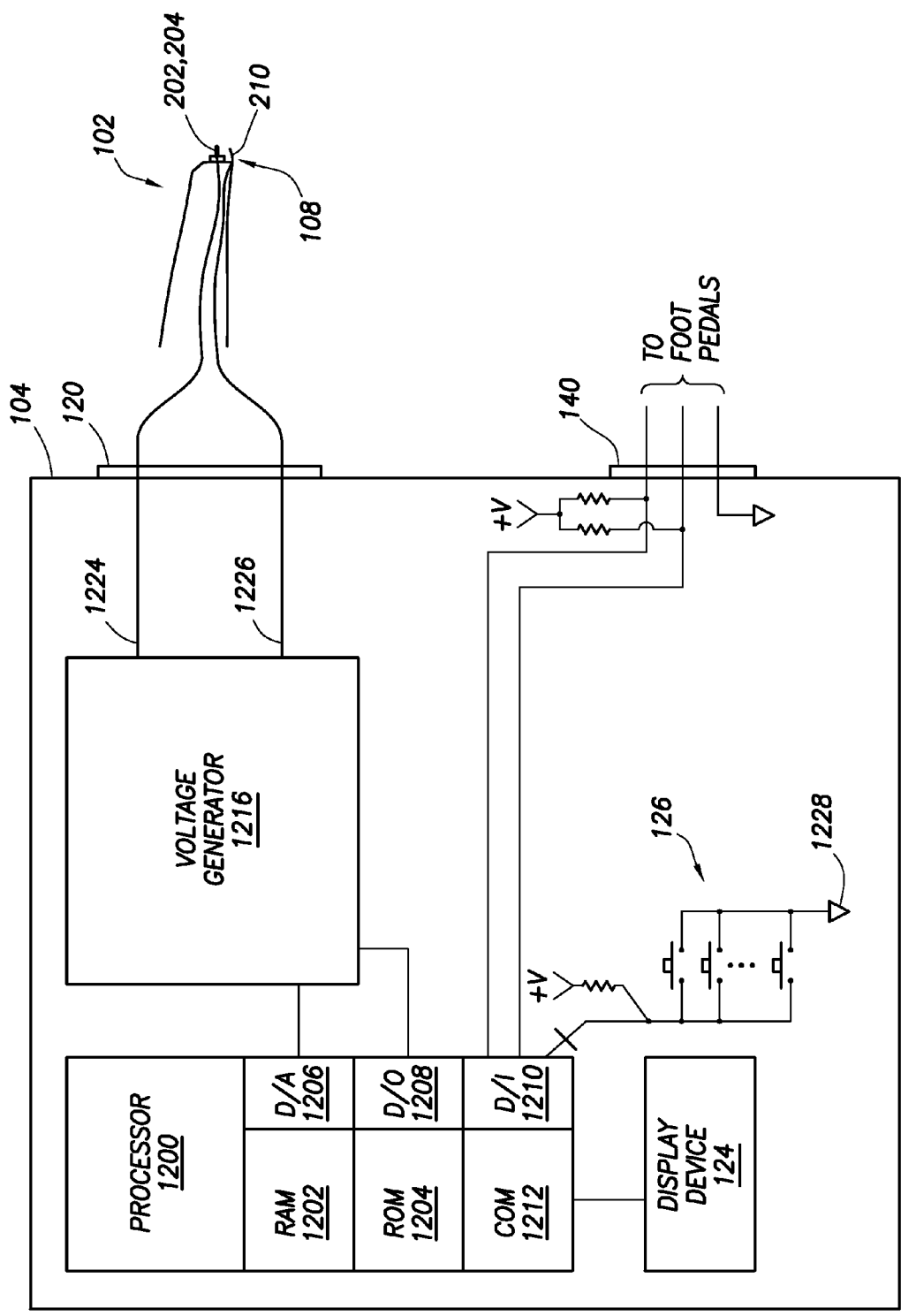
Figure 13:
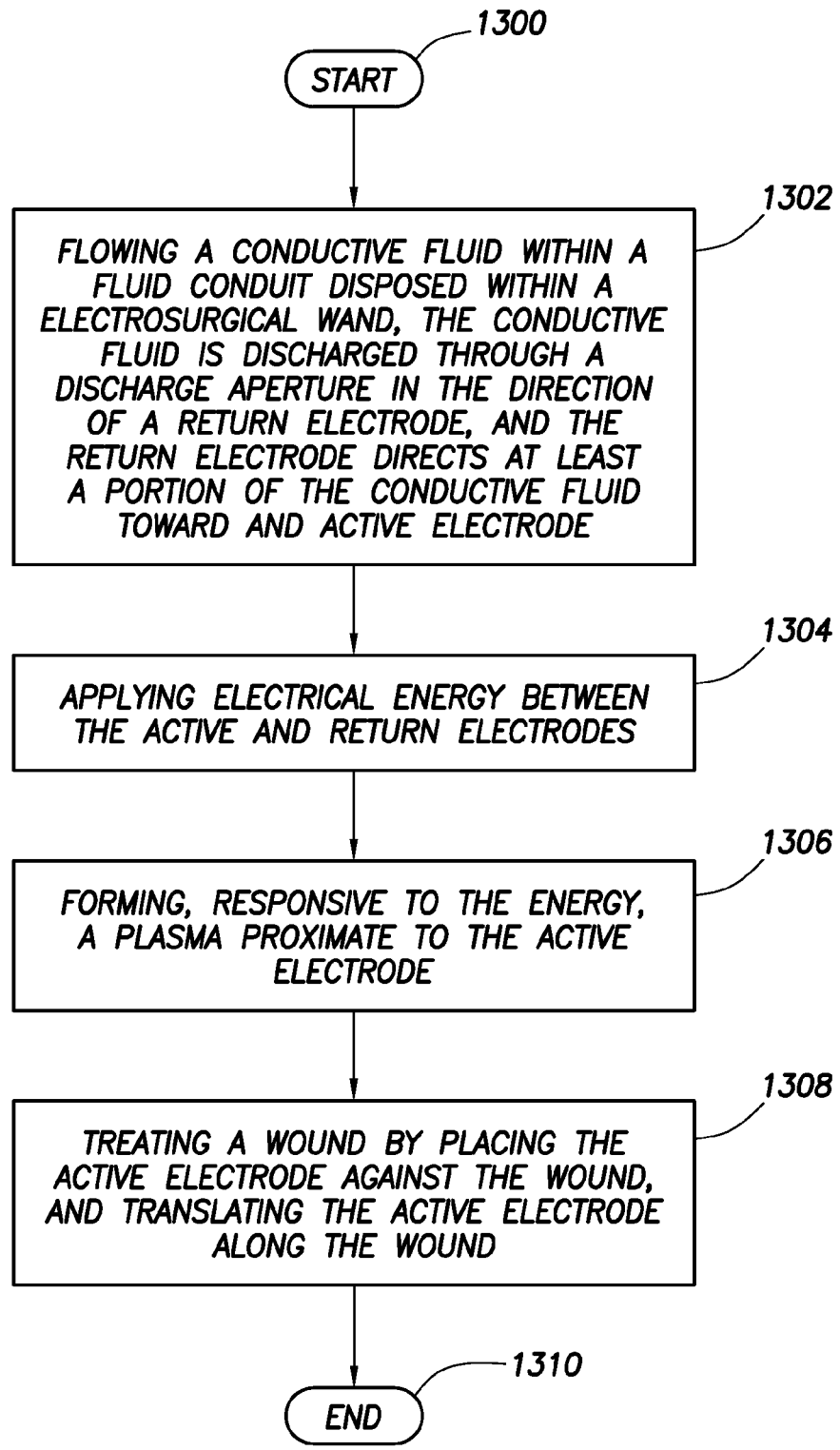

FIG. 12 shows an electrical block diagram of an electrosurgical controller in accordance with at least some embodiments; and FIG. 13 shows a method in accordance with at least some embodiments.

NOTATION AND NOMENCLATURE

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow return path with respect to an active electrode, and/or an electrode of an electrical surgical wand which does not itself produce an electrically-induced tissue-altering effect on tissue targeted for treatment.

A fluid conduit said to be "within" an elongate housing shall include not only a separate fluid conduit that physically resides within an internal volume of the elongate housing, but also situations where the internal volume of the elongate housing is itself the fluid conduit.

"Abut" and "abutting" shall mean that two items are adjacent, but shall not be read to require that two items actually touch.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Figure 1:
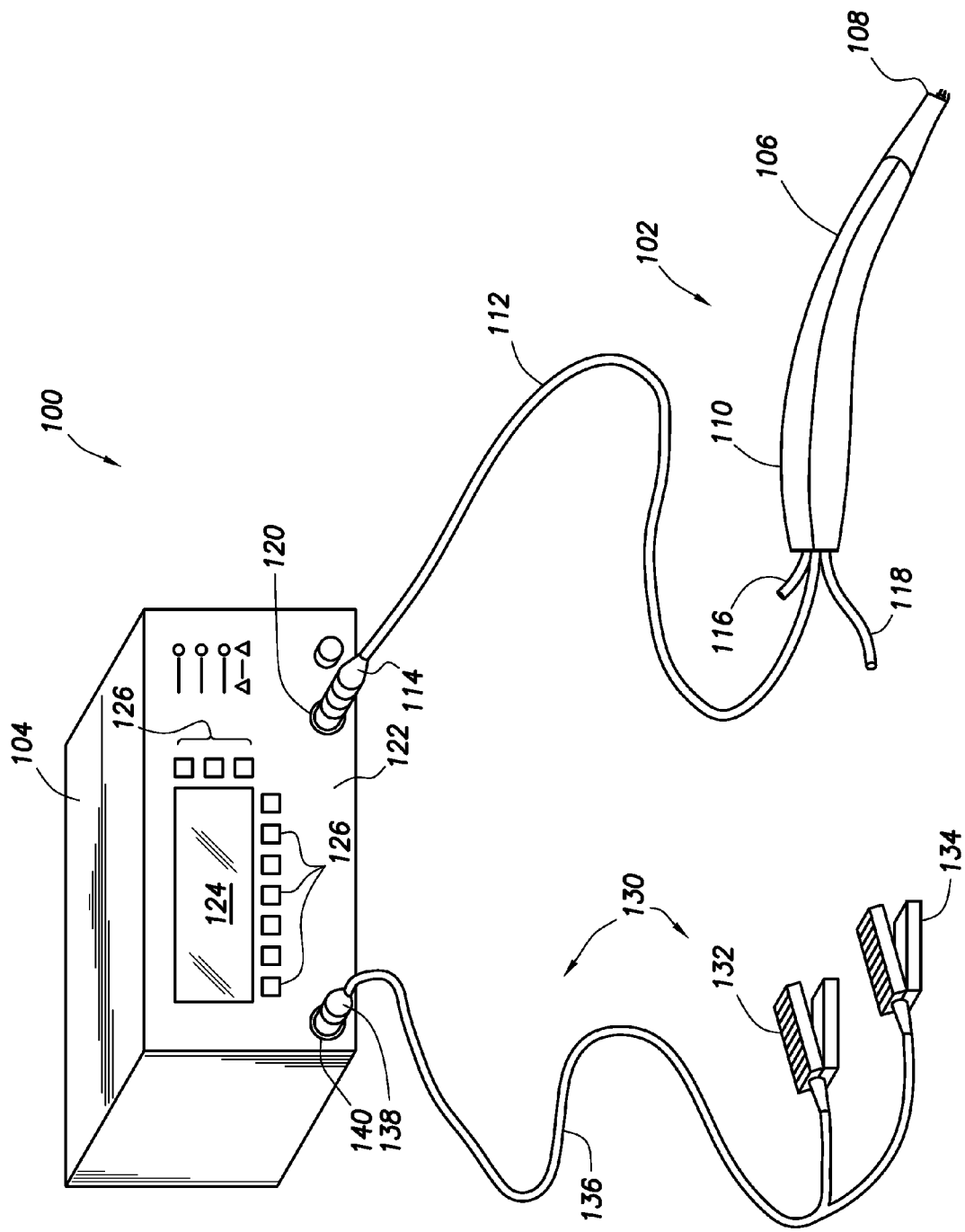
FIG. 1 shows an electrosurgical system in accordance with at least some embodiments.

FIG. 1 illustrates an electrosurgical system 100 in accordance with at least some embodiments. In particular, the electrosurgical system comprises an electrosurgical wand 102 (hereinafter "wand") coupled to an electrosurgical controller 104 (hereinafter "controller"). The wand 102 comprises an elongate housing 106 that defines distal end 108 where at least some electrodes are disposed. The elongate housing 106 further defines a handle or proximal end 110. The wand 102 further comprises a flexible multi-conductor cable 112 housing a plurality of electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a first flexible tubular member 116 and a second flexible tubular member 118. In some embodiments, the flexible tubular member 116 is used to provide saline to the distal end 108 of the wand. Likewise in some embodiments, flexible tubular member 118 is used to provide suction for aspiration at the distal end 108 of the wand. In some embodiments, the flexible tubular member 116 is a hose having a 0.152 inch outside diameter, and a 0.108 inch inside diameter, but other sizes may be equivalently used. Further, in some embodiments the flexible tubular member 118 is a hose having a 0.25 inch outside diameter, and a 0.17 inch internal diameter, but other sizes may be equivalently used.

Still referring to FIG. 1, the controller 104 controllably provides energy to the wand 102 for the electrosurgical procedures (discussed more below). A display device or interface panel 124 is visible through the outer surface 122 of the controller 104, and in some embodiments a user may select operational modes of the controller 104 by way of the interface device 124 and related buttons 126.

In some embodiments the electrosurgical system 100 also comprises a foot pedal assembly 130. The foot pedal assembly 130 may comprise one or more pedal devices 132 and 134, a flexible multi-conductor cable 136 and a pedal connector 138. While only two pedal devices 132, 134 are shown, one or more pedal devices may be implemented. The outer surface 122 of the controller 104 may comprise a corresponding connector 140 that couples to the pedal connector 138. The foot pedal assembly 130 may be used to control various aspects of the controller 104, such as the operational mode. For example, a pedal device, such as pedal device 132, may be used for on-off control of the application of radio frequency (RF) energy to the wand 102. A second pedal device, such as pedal device 134, may be used to control and/or set the operational mode of the electrosurgical system. For example, actuation of pedal device 134 may switch between energy levels. In yet still further embodiments, the wand 102 may further comprise switches accessible on an outside portion, where the switches may control the operational modes of the controller 104.

The electrosurgical system 100 of the various embodiments may have a variety of operational modes. One such mode employs Coblation® technology. In particular, the assignee of the present disclosure is the owner of Coblation® technology. Coblation® technology involves the application of an RF energy between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region near the one or more active electrodes and the target tissue. Electrically conductive fluid may be inherently present in the body, such as blood, puss, or in some cases extracellular or intracellular fluid. In other embodiments, the electrically conductive fluid may be a liquid or gas, such as isotonic saline. In a particular embodiment of wound treatment, the electrically conductive fluid is delivered in the vicinity of the active electrode and/or to the target site by the wand 102, such as by way of the internal fluid conduit and flexible tubular member 116.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation® mode, the electrosurgical system 100 of FIG. 1 may also in particular situations be useful for sealing blood vessels, when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may have a coagulation mode where RF energy at a second, lower voltage is applied to one or more active electrodes sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue.

A more complete description of the various phenomena can be found in commonly assigned U.S. Pat. Nos. 6,355,032; 6,149,120 and 6,296,136, the complete disclosures of which are incorporated herein by reference.

Figure 2A:
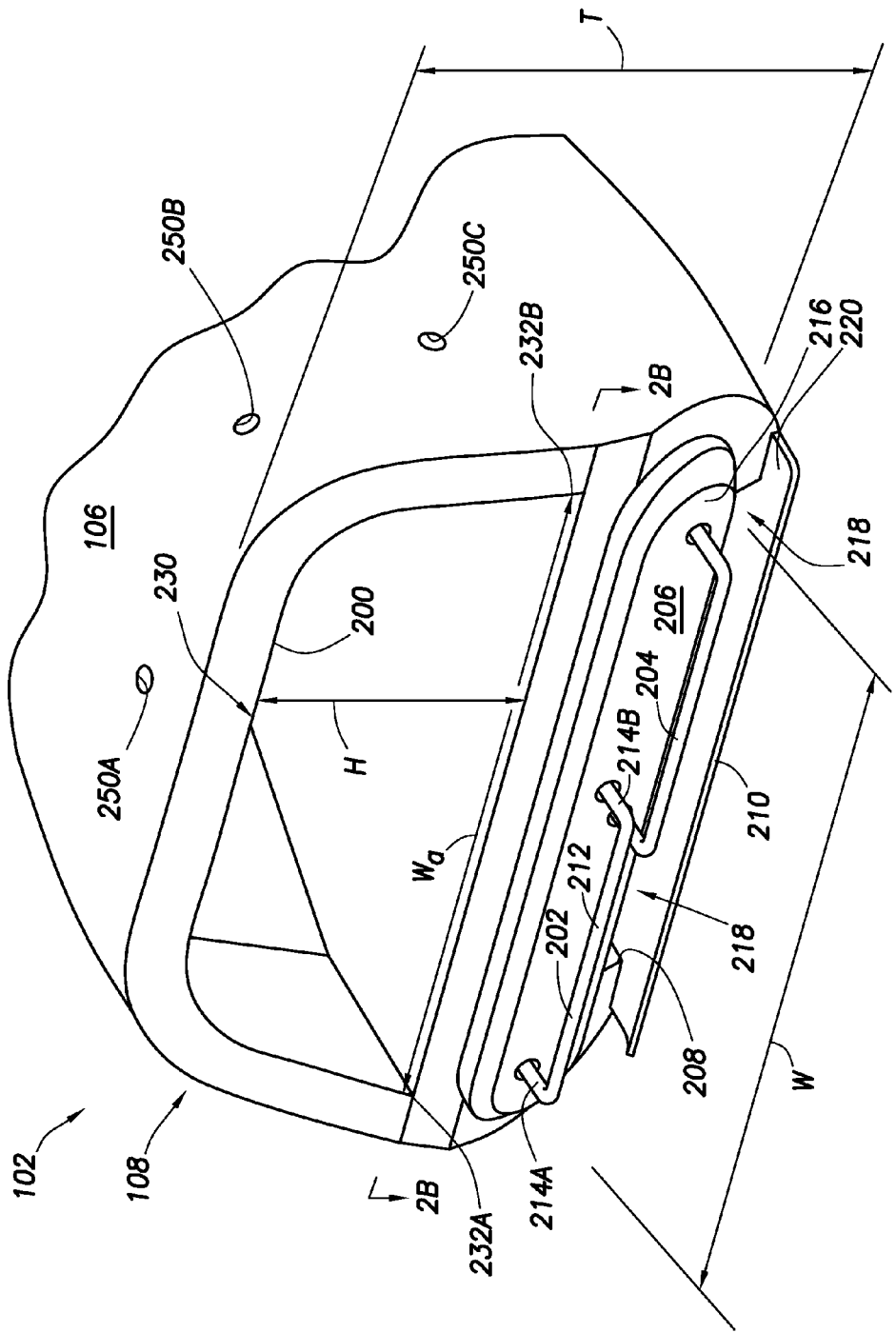
FIG. 2A shows a perspective view a portion of a wand in accordance with at least some embodiments.

FIG. 2A illustrates a perspective view of the distal end 108 of wand 102 in accordance with at least some embodiments. In particular, the illustrative system of FIG. 2 has an aspiration aperture 200, two active electrodes 202 and 204, a support member 206, a discharge aperture 208, and return electrode 210. Moreover, the illustrative distal end 108 defines a width (labeled W in the figure) and a thickness (labeled T in the figure). Each of the components will be discussed in turn.

The support member 206 is coupled to the elongate housing 106. In a particular embodiment, the elongate housing 106 and handle 110 (FIG. 1) are made of a non-conductive plastic material, such as polycarbonate. In yet other embodiments, the handle 110 and/or elongate housing 106 may be constructed in whole or in part of metallic material, but the metallic material is non-grounded and/or does not provide a return path for electrons to the controller 104. Further, support member 206 is a non-conductive material resistant to degradation when exposed to plasma. In some cases support member 206 is made of a ceramic material (e.g., alumina ceramic), but other non-conductive materials may be equivalently used (e.g., glass).

An illustrative two active electrodes 202 and 204 are coupled to the support member 206. Each active electrode is a metallic structure, around which plasma is created during use in some operational modes. In some case, the wire is stainless steel, but other types of metallic wire (e.g., tungsten, molybdenum) may be equivalently used. As illustrated, each active electrode 202 and 204 is a loop of wire having a particular diameter. Smaller diameter wire for the active electrodes advantageously results in less thermal heating of the tissue, but there is a tradeoff with wire strength, as smaller wire diameters tend to break and/or bend more easily. In some embodiments, the wire diameter for each active electrode is between and including 0.008 and 0.015 inches, and in a particular case 0.010 inches. Using active electrode 202 as exemplary of both active electrodes, the illustrative active electrode 202 comprises a straight portion 212, as well as two standoff portions 214 (labeled 214A and 214B). In accordance with at least some embodiments, the length of the straight portion 212 (i.e., standoff distance) is between and including 0.16 and 0.18 inches. Moreover, standoff portions 214 define an exposed length of between and including 0.010 and 0.050 inches, and in some cases between and including 0.015 and 0.025 inches. In these embodiments the length defined by the standoff portions 214 is measured from the surface 216 of the support member 206 to the central axis of the straight portion 202. It will be understood, however, that the standoff portions 214 may extend into the support member 206, and thus will be longer than the exposed length. For the example wire diameters and lengths of this paragraph, the exposed surface area of each active electrode (i.e., that portion residing outside the non-conductive support member 206) may be between and including 0.00447 and 0.04141 square inches.

Still referring to active electrode 202 as illustrative of both active electrodes, the active electrode 202 is electrically coupled to the controller 104 (FIG. 1). In some cases, the active electrode 202 is coupled to the controller by way of one of the standoff portions 214 and an insulated conductor (not specifically shown) that runs through the elongate housing 106. Thus, by way of the cable 112 (FIG. 1) and electrical pins (shown in FIG. 10 below) in the connector 114 (FIG. 1), the active electrode 202 couples to the controller 104 (FIG. 1). In some cases the active electrodes all couple to the controller 104 by way of the same electrical pin, and in other cases each active electrode may couple to the controller by way of its own electrical pin.

The straight portions of the active electrodes in FIG. 2A are parallel. However, the arrangement of FIG. 2A is merely illustrative. The active electrodes may take any suitable shape, and any suitable orientation between them. For example, the straight portions of the active electrodes may be coaxial. Further still, straight portions of the active electrodes may form an obtuse angle. Yet further still, the active electrodes may take any suitable form, such as a sinusoid between the standoffs 214, or saw tooth pattern between the standoffs 214. In many cases, regardless of the form of the active electrodes, each active electrode 202 and 204 has approximately the same standoff distance from a plane defined by the outer surface 216 of the support member 214.

FIG. 2A further shows a discharge aperture 208. The discharge aperture 208 as illustrated is rectangular, where the long dimension is aligned with the width W. Rectangular shaped discharged apertures are merely illustrative, and any suitable shape may be equivalently used (e.g., circular, oval, square). Within the distal end 108 the aperture 208 defines a fluid conduit 218. The fluid conduit is fluidly coupled within the elongate housing 106 to flexible tubular member 116

(FIG. 1), through which conductive fluid is pumped or gravity fed during use. Thus, during use, conductive fluid flows into the flexible tubular member 116 (FIG. 1), through one or more fluid conduits (not specifically shown) within the elongate housing 106, through the fluid conduits 218, and out of the discharge aperture 208.

In the various embodiments, the conductive fluid has conductivity above a minimum threshold. More particularly, the conductive fluid will have conductivity greater than 0.2 milli-Siemens per centimeter (mS/cm), in some cases greater than about 2 mS/cm, and in other cases greater than about 10 mS/cm. An example of the conductive fluid that may be used is isotonic saline, having conductivity of about 17 mS/cm. During wound debridement, saline may flow at the rate of between and including 30 and 70 milli-Liters per min (mL/min), but may vary depending on factors such as: the pressure at the aspiration aperture 200; the geometry, material property and configuration of the return electrode (discussed below); the geometry, material properties and configuration of the active electrodes 202 and 204; and the geometry, material properties and configuration of the support member 206.

The distal end 108 of the wand 102 further comprises a return electrode in the form of a conductive plate 210. In particular, the conductive plate 210 abuts the discharge aperture 208, and in the embodiments of FIG. 2A a portion of the conductive plate 210 at least partially defines the discharge aperture 210. Further as shown, the conductive plate 210 abuts the discharge aperture on an opposite side of the discharge aperture than the active electrodes 202 and 204 and the support member 206. For reasons discussed more below, at least a portion of the conductive plate resides over the discharge aperture 208. "Over" in this instance does not imply an orientation of the distal end 108 of the wand 102; rather, "over" is only meant to imply that if the fluid conduit 218 defined by the discharge aperture 208 was projected outward past the discharge aperture 208, at least a portion of the conductive plate 210 would reside within the projected area.

The conductive plate 210 is made of conductive material, which conductive material forms a return path for electrical current associated with energy applied to the active electrodes. In some cases the conductive plate 210 is made of stainless steel, but other types of metals (e.g., tungsten, molybdenum) may be equivalently used. The illustrative conductive plate 210 is oriented such that at least some of the conductive fluid flowing through the fluid conduit 218 contacts the conductive plate 210 before contacting an adjacent wound or contacting the active electrodes 202 and 204. For the particular embodiment of the conductive plate 210 forming at least a portion of the fluid conduit 218 through which the conductive fluid flows, the upper (in the view of FIG. 2) surface 220 of the conductive plate 210 defines an exposed surface area of greater than the exposed surface areas of the active electrodes. In some embodiments the exposed upper surface 220 of the conductive plate 210 is at least twice the exposed surface area of the active electrodes, and in yet still other embodiments the exposed upper surface 220 of the conductive plate 210 is at least eight times the exposed surface area of the active electrodes.

Conductive plate 210 is electrically coupled to the controller 104 (FIG. 1). In some cases, the conductive plate 210 is coupled to the controller by way of an insulated conductor (not specifically shown) that runs through the elongate housing 106. Thus, by way of the cable 112 (FIG. 1) and electrical pins (shown in FIG. 10 below) in the connector 114 (FIG. 1), the conductive plate 210 couples to the controller 104 (FIG. 1).

Having the conductive plate 210 at least partially define the fluid conduit 218, and further having the conductive plate 210 oriented in such a way that conductive fluid exiting the discharge aperture 208 encounters the conductive plate 210 and aids in operation of the wand 102 for wound care in several ways. First, having the conductive plate 210 at least partially form the fluid conduit 218 increases the likelihood that the conductive fluid used to wet the electrodes makes good contact with the conductive plate 210 operated as a return electrode. Stated otherwise, regardless of the orientation of the wand 102 with respect to gravity, the conductive fluid provided to the wound treatment site has a better chance of contacting the conductive plate 210 operated as a return electrode due at least in part to the orientation of the conductive plate 210 relative to the discharge aperture 208. Second, the conductive plate 210 residing over the discharge aperture 208 helps direct the flowing conductive fluid toward the active electrodes 202 and 204.

FIG. 2A also illustrates that a wand 102 in accordance with at least some embodiments further comprises an aspiration aperture 200. The aspiration aperture 200 is fluidly coupled to the flexible tubular member 118 (FIG. 1) by way of a lumen or fluid conduit (not specifically shown) within the wand 102. Thus, and as the name implies, the aspiration aperture 204 is used to remove byproducts of wound treatment using the wand 102, such as removal of excess conductive fluid, molecularly disassociated tissue, and tissue separated from the wound but otherwise still intact. As illustrated, the aspiration aperture 200 has width approximately the same as the support member 206, and thus slightly wider than the active electrodes. In some cases, the width of the aspiration aperture 200 (the width labeled "$W_a$") may be 0.591 inches (about 15 millimeters (mm)) or less, in some case 0.394 inches (about 10 mm), and in other cases 0.197 inches (about 5 mm), depending on the width of the distal end 108 of the wand and/or the number of active electrodes. Moreover, in some embodiments the height "H" of the aspiration aperture is a function of the standoff distance of the active electrodes. In some cases the height H may be greater than or equal to three times (i.e., 3 to 1) the exposed length of the standoff portions, in other cases greater than or equal to six times (i.e., 6 to 1) the exposed length of the standoff portions, and in yet further cases greater than or equal to ten times (i.e., 10 to 1) the exposed length of the standoff portions. For example, with an exposed length of the standoff portions being in the range 0.015 to 0.025 inches, and a 6-to-1 relationship, the aspiration aperture height may be on the order 0.01 to 0.177 inches, respectively.

In operation of the various embodiments, aggressive aspiration is contemplated to help remove larger pieces of tissue detached via the ablative process but not molecularly disassociated (discussed more below). In some cases, the aspiration may be created by an applied pressure between and including 100 millimeters of mercury (mmHg) and 400 mmHg below atmospheric. However, in some cases aggravation of an existing wound may occur if the aspiration aperture 200 is allowed to seal against the wound. In order to reduce the possibility of the aspiration aperture 200 sealing against the wound and/or patient, and as illustrated, in some embodiments at least a portion of the aspiration aperture is closer to the handle 110 (FIG. 1) than any portion of the discharge apertures. In particular, portion 230 is closer to the handle than portions 232A and 232B. Thus, when the distal end 108 is held in an orientation where the active electrodes 202 and 204 can interact with the wound, the likelihood of the aspiration aperture 200 sealing against the wound and/or patient is drastically reduced. In yet still further embodiments, optional apertures 250 (three illustrative apertures labeled 250A through 250C) may be implemented to ensure that if, by chance, the aperture 200 seals against the wound, the wound will not by subjected to the full force of the aspiration suction as air may flow into the apertures 250.

Figure 2B:
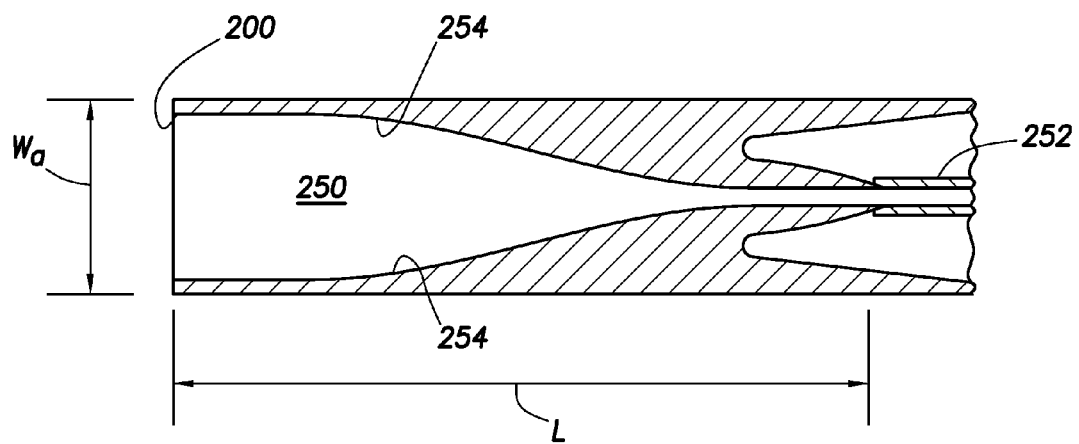
FIG. 2B shows a cross-sectional view taken substantially along line 2B-2B of FIG. 2A.

FIG. 2B shows an overhead cross-sectional view of the wand taken substantially along lines 2B-2B of FIG. 2A. In particular, FIG. 2B shows the aspiration aperture 200 as well as a fluid conduit 250. In operation, suction is provided to the flexible tubular member 118 (FIG. 1), and flexible tubular member 118 either extends into the internal volume of the wand 102 to become, or fluidly couples to, internal lumen 252. Thus, conductive fluid, molecularly disassociated tissue, as well as tissue pieces (discussed more below), are drawn through the aspiration aperture 200, into the fluid conduit 250, and eventually into the lumen 252. The inventors of the present specification have found that particular lengths of the fluid conduit 250 between aspiration aperture 200 and the entrance to the internal lumen 252 work better than others. For example, if the length is too short, the fluid conduit 250 is subject to clogging. Likewise, if the length is too long, zones of little or no airflow develop, again leading to clogs. In accordance with at least some embodiments the length of the fluid conduit 250 between the aperture 200 and the entrance to the internal lumen 252 is a function of the width $W_a$ of the aspiration aperture at the widest point. More particularly, in accordance with at least some embodiments the internal walls 254 that define the fluid conduit 250 should be smoothly varying, and the length over which the width changes should be at least two times the change in width, and in most cases not longer than eight times the change in width. Consider, as an example, a wand where the $W_a$ is 0.39 inches (about 10 millimeters (mm)), and the internal diameter of the lumen 252 is 0.118 inches (3 mm). In such a situation the change in internal width of the fluid conduit 250 between the aspiration aperture 200 and the entrance to the lumen 252 will be about 0.272 inches (about 7 mm), and in at least some embodiments the length L over which the change in width is implemented should be at least 0.544 inches (at least 14 mm). In a particular embodiment the change in internal diameter to the length L is related as:

$$L=(W_a-ID)*2.3 \quad (1)$$

where ID is the internal diameter of the lumen 252. Thus, for example, a fluid conduit 270 associated with an aspiration aperture in operational relationship to a wand 102 with a single active electrode will have a shorter length than in the transition to the internal lumen than a fluid conduit 270 associated with an aspiration aperture in operational relationship to a wand 102 with three or more active electrodes.

The inventors of the present specification present the characteristic of the length L of FIG. 2B in terms of the width $W_a$ of the aspiration aperture for sake of simplicity. Further, equivalent, relationships may be determined, for example, based on changes in cross-sectional area of the fluid conduit 250 taking into account the height H (FIG. 2A) in relation to the standoff distances implemented by the standoff portions 214. Moreover, while FIG. 2B shows each wall 254 of the fluid conduit 250 to be smoothly varying similar to a tangent function (i.e., asymptotically approaching the $W_a$ on one end, and asymptotically approaching the internal diameter of the lumen 252 on the other), other smoothly varying internal surfaces may be equivalently used (e.g., straight line change in $W_a$ from the aperture 200 to the internal diameter of the lumen 252, asymptotically approaching the internal diameter of the lumen 252).

Figure 3:
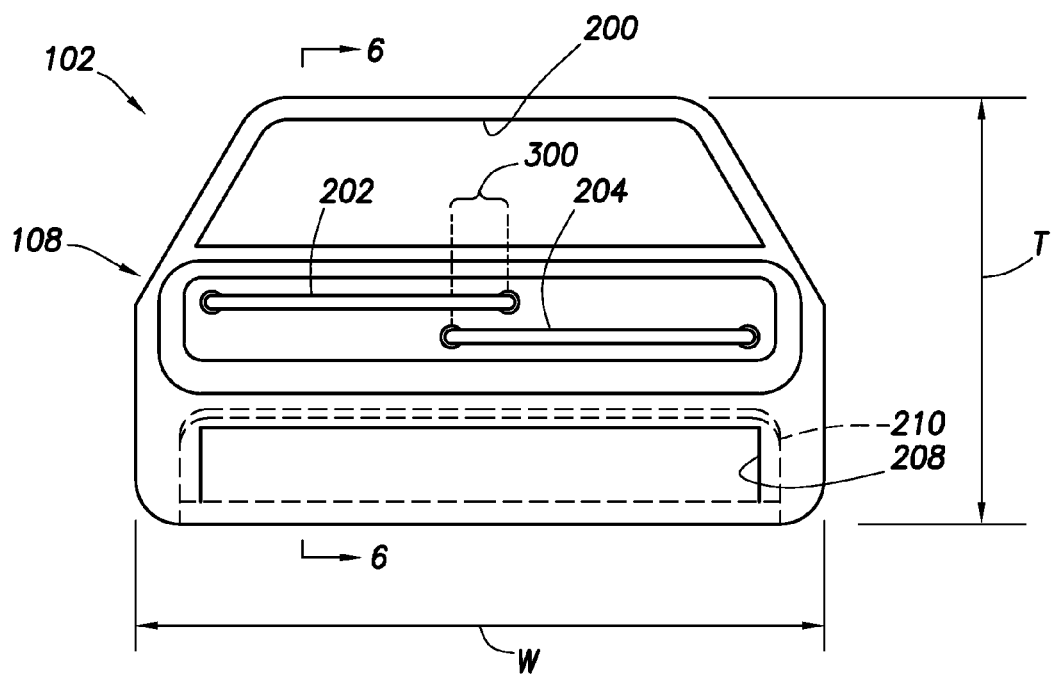
FIG. 3 shows a front elevation view of a wand in accordance with at least some embodiments.

FIG. 3 shows a front elevation view of the distal end 108 of the wand 102 in accordance with at least some embodiments. In the view of FIG. 3, the conductive plate 210 is transparent (i.e., shown in dashed form) so that the structural relationship behind (in this view) the conductive plate 210 may be seen. In particular, the view of FIG. 3 shows that the distal end of the conductive plate 210 resides over or occludes the discharge aperture 208, and in this case distal end of the conductive plate 210 occludes the full area of the discharge aperture 208. In other cases, the distal end of the conductive plate 210 occludes between half and the full area of the discharge aperture 208. Stated a different way, if the discharge aperture 208 resides in and defines a plane (in this view, the plane defined by the page), then when viewed perpendicularly to the plane defined by the discharge aperture 208, the conductive plate 210 occludes more than half an area defined by the discharge aperture. Thus, as conductive fluid is discharged through the discharge aperture 208, the chance the conductive fluid makes good electrical contact with the conductive plate 210 is high, regardless of the orientation of the wand 102 in relation to gravity.

FIG. 3 also shows a relationship between the active electrodes in accordance with at least some embodiments. In particular, in accordance with some embodiments the active electrodes 202 and 204 are offset along the thickness T. For example, as shown active electrode 202 is closer to the aspiration aperture 200 than active electrode 204. While in some embodiments the active electrodes have the same elevation with respect to the thickness T, in the illustrative embodiments where an offset is present there is an overlap 300 of the active electrodes. The overlap 300 of the active electrodes ensures that, in operation, the surface left within the wound is less likely to have any ridges or elevation changes caused by non-uniformity of the active electrodes.

Figure 4:
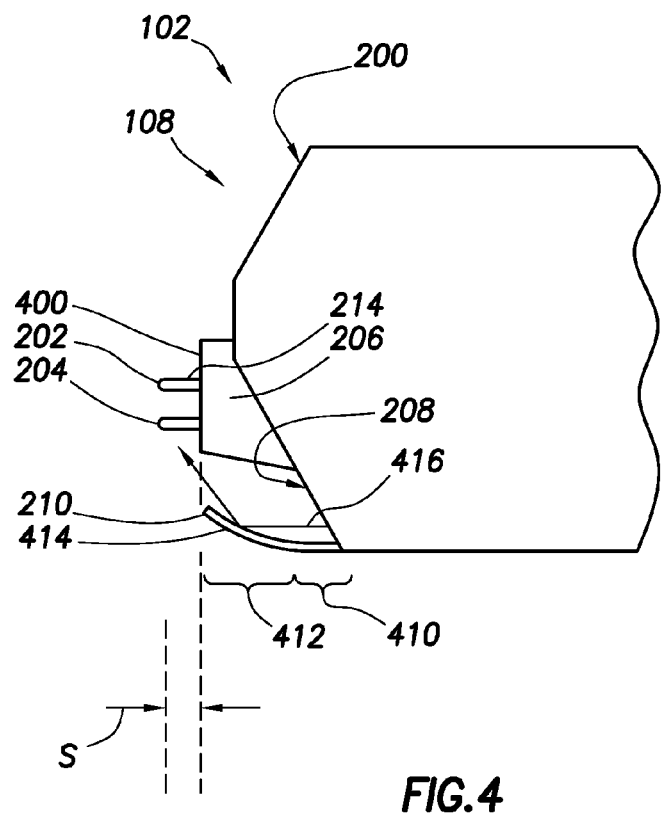
FIG. 4 shows a side elevation view of a wand in accordance with at least some embodiments.

FIG. 4 shows a side elevation view of the distal end 108 of a wand 102 in accordance with various embodiments. In the view of FIG. 4, the offset of the active electrodes 202 and 204 to enable the overlap 300 (not shown in FIG. 4) is visible. In particular, active electrode 202 is offset toward the aspiration aperture 200, while the active electrode 204 is offset toward the discharge aperture 208. The offset of the active electrodes 202 and 204 shown in FIG. 4 is merely illustrative, and the offsets may be equivalently swapped. Further, while FIG. 4 shows the active electrodes 202 and 204 to be parallel, other embodiments, including embodiments with overlap, may be fashioned where the outer portions of the active electrodes form an angle of greater or lesser than 180 degrees.

FIG. 4 also shows standoff distances of the active electrodes 202 and 204. In particular, while the front face 400 of the support member 206 defines a plane, and the standoff portions 214 define exposed length such that the straight portion of each active electrode 202 and 204 has a standoff distance (the standoff labeled "S" in FIG. 4) from the front face 400 that is approximately the same (i.e., the same within manufacturing tolerances).

FIG. 4 also shows aspects of directing conductive fluid toward the active electrodes by the conductive plate. In particular, the conductive plate 210 of FIG. 4 has a straight portion 410 and a lip portion 412 on the distal end of the conductive plate 210. The lip portion 412 is disposed over the discharge aperture 208. In the illustrative case of FIG. 4, the lip portion 412 is formed by a curved portion 414 on the distal end of the conductive plate. The lip portion 412 acts to direct conductive fluid discharged from the discharge aperture 208 toward the active electrodes, as illustrated by arrow 416. That is, the conductive fluid exits the discharge aperture 208 and encounters the lip portion 412. The lip portion 412 is designed and constructed to change the flow direction of at least some of the conductive fluid to flow more directly towards the active electrodes. Thus, not only does the conductive fluid fully "wet" the conductive plate 210 acting as a return electrode, but the likelihood of "wetting" the active electrodes is increased as well, independent of the orientation of the wand 102 in relation to gravity. Moreover, FIG. 4 illustrates that in some embodiments the distal end of the conductive plate 210 extends no further than the plane defined by the front face 400.

Figure 5:
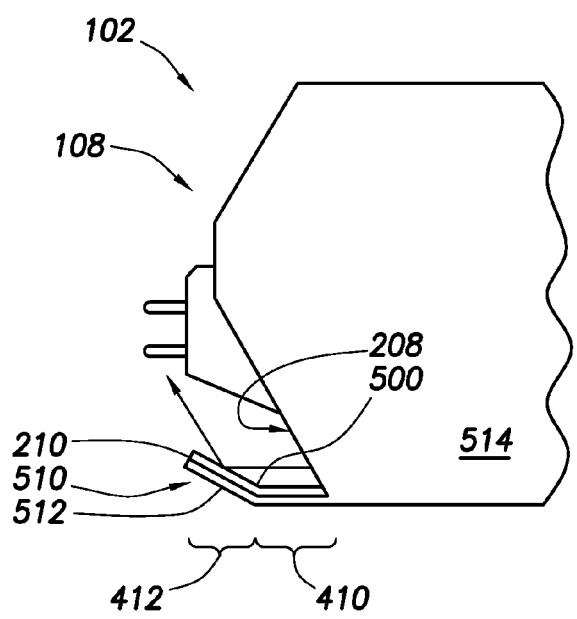
FIG. 5 shows a side elevation view of a wand in accordance with at least some embodiments.

FIG. 5 shows a side elevation view of the distal end 108 of a wand 102 in accordance with other embodiments. In particular, FIG. 5 shows an alternative arrangement of the conductive plate 210. The conductive plate 210 of FIG. 5 has the straight portion 410 and the lip portion 412, but in the illustrated embodiments the lip portion 412 is formed by a bend 500 in a medial portion of the conductive plate 210. Consider that if the lip portion 412 defines a plane, the angle between the plane created by the lip portion and the discharge aperture 208 is an acute angle. Although the mechanical relationship of the conductive plate 210 differs from that of FIG. 4, the outcome in a conductive fluid flow sense is the same. That is, conductive fluid exiting the discharge aperture 208 encounters the lip portion 412, and is directed toward the active electrodes 202 and 204. Thus, both the conductive plate 210 acting as a return electrode, and the active electrodes 202 and 204, have a better chance of being fully "wetted" for purposes of plasma creation.

FIG. 5 also illustrates that in some embodiments the conductive plate 210 is insulated on a side opposite the discharge aperture 208 (i.e., the bottom side 510). In particular, the conductive plate 210 is covered on the bottom side 510 with an insulating material 512. In some cases the insulating material is an extension of the non-conductive outer housing 514. In other embodiments, the insulating material 512 may be any non-conductive or partially non-conductive material. For example, the conductive plate 210 could be anodized, dipped in an insulating material, have an insulating material glued thereon, and the like. The embodiments with insulating material 510 are not limited to embodiments where the lip portion 412 is created by a bend 500. The insulating material 512 may be used with any configuration of the conductive plate 210. Additionally, in any configuration of conductive plate 210, the bottom side 510 may act as a guide surface that engages the tissue to be treated as the wand is translated across the wound.

Figure 6:
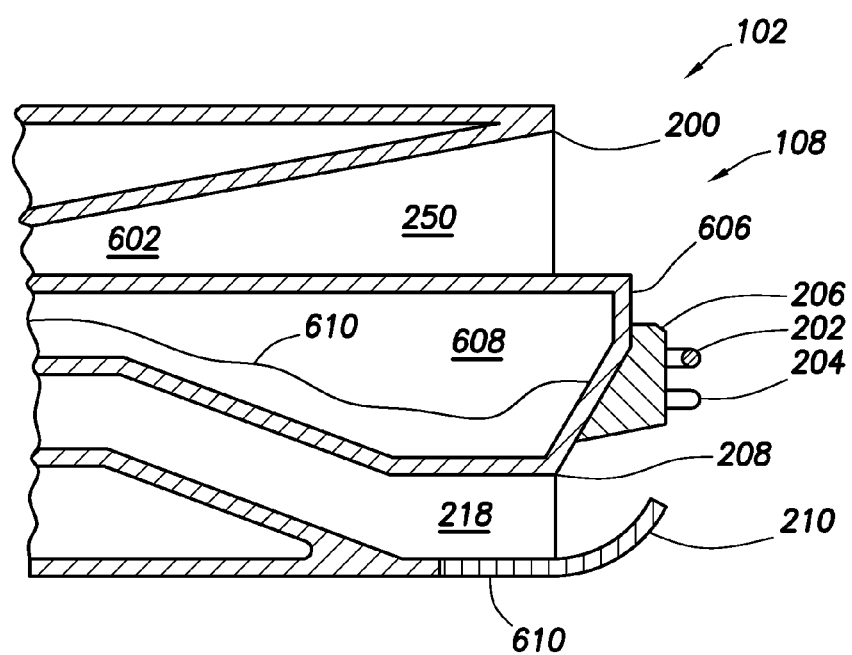
FIG. 6 shows a cross-sectional view taken substantially along line 6-6 of FIG. 3.

FIG. 6 shows a cross-sectional elevation view of the distal end 108 of the wand 102 taken substantially along line 6-6 of FIG. 3. In particular, FIG. 6 shows that, in accordance with some embodiments, the aspiration aperture 200 defines a wide opening, but the fluid conduit 250 within the distal end tapers downward to a narrower conduit 602. However, in other embodiments (e.g., as shown in FIG. 2B) a lumen may reside within the elongate housing 106 and fluidly couple to the fluid conduit 250. FIG. 6 further illustrates the support member 206 coupled to an outer face 606 of the distal end 108 of the wand 102. In these embodiments, the support member 206 may couple by any suitable means, such as an adhesive. In other cases, the support member 206 and distal end of the elongate housing may have mating mechanical features that fully or partially retain the support member 206. Moreover, the distal end 108 defines a cavity region 608 between the fluid conduit 250 associated with the aspiration aperture 200, and the fluid conduit 218 associated with the discharge aperture 208. Within the cavity 608 may reside one or more electrical leads 610 that electrically couple the active electrodes 202 and 204 to the controller. Though not visible in the view of FIG. 6, the cavity 608 may also contain an electrical lead that electrically couples the conductive plate 210 to the controller.

FIG. 6 also illustrates that, in at least some embodiments, the fluid conduit 218 associated with the discharge aperture 208 is partially defined by the conductive plate 210. In particular, in the illustrated embodiments portion 610 of conductive plate 210 extends into and at least partially defines the fluid conduit 218. In this way, the conductive fluid flowing in the fluid conduit contacts the conductive plate 210 acting as a return electrode even before being discharged through the discharge aperture 208. In other embodiments, the fluid conduit 218 may be fully defined by the material that makes up the elongate housing 106 (e.g., polycarbonate), and the conductive plate 210 may be positioned in such a way that the conductive fluid does not contact the conductive plate until after the fluid has discharged through the discharge aperture 208.

Figure 7:
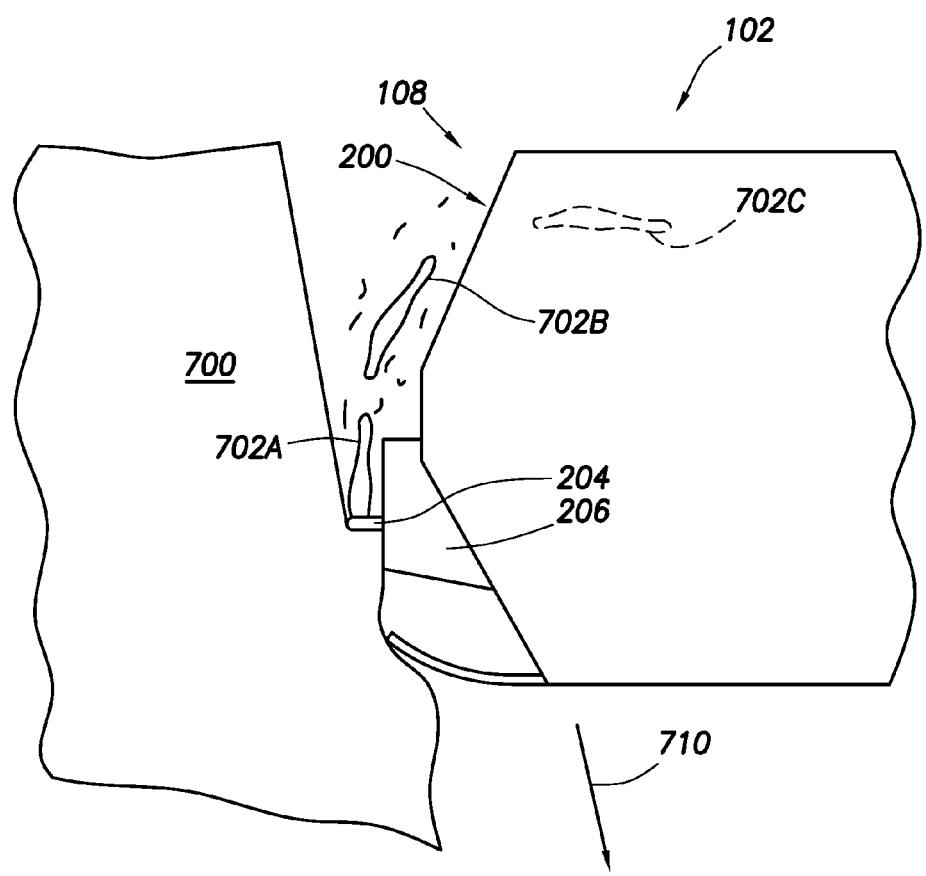
FIG. 7 a side elevation view of a wand in operational relationship to a wound in accordance with at least some embodiments.

FIG. 7 shows a side elevation view of the distal end 108 of wand 102 in use for wound care. In particular, the wand 102 is shown abutting wound 700, such as a diabetic foot ulcer. In operation, electrical energy is applied to the active electrodes, but here only active electrode 204 is visible. The energy in the example of FIG. 7 is sufficient to create plasma near the active electrodes, which thus molecularly disassociates tissue that comes in relatively close contact with the active electrodes. However, the arrangement of the active electrodes is such that the reach of the plasma is less than the standoff distance of each active electrode from the plane defined by the front face of the support member 206. Thus, when operated with sufficient energy to create plasma, as the wand is translated along the wound (as illustrated by arrow 710) the active electrodes act to slice portions of the tissue via the plasma-mediated ablative process, rather than attempting to completely molecularly disassociate the tissue. The result is strips of tissue 702 (multiple strips labeled 702A through 702C) are created, and which strips of tissue 702 (as well as conductive fluid and remnants of tissue molecularly disassociated) are drawn into the aspiration aperture 200 by the aspiration action. The inventors of the present specification have found that the situation illustrated by FIG. 7 is particularly efficient at debridement of wounds (e.g., removing biofilm). While not wanting to be tied to any particular theory of why the treatment works well, it is believed that the plasma created by the wand 102 is particularly efficient at destroying bacteria. Moreover, it is believed that the "slicing" action in combination with the aggressive aspiration helps ensure that the potentially bacteria contaminated strips of tissue 702 either: do not contact the remaining wound portions after removal because of motion and aspiration (thus reducing the chances of re-infecting the wound); or, if contact is present, that the contact is for such a short duration, or the contact is on side of the strips of tissue where bacteria have been killed by the plasma, that the chances of re-infection of the wound 700 are low.

Figure 9:
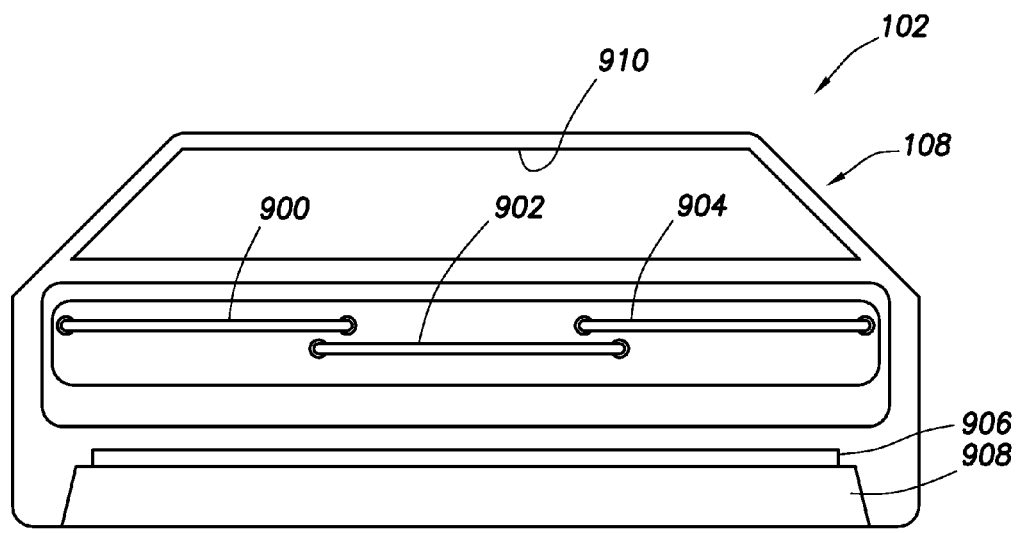
FIG. 9 shows a front elevation view of a wand in accordance with at least some embodiments.
Figure 8:
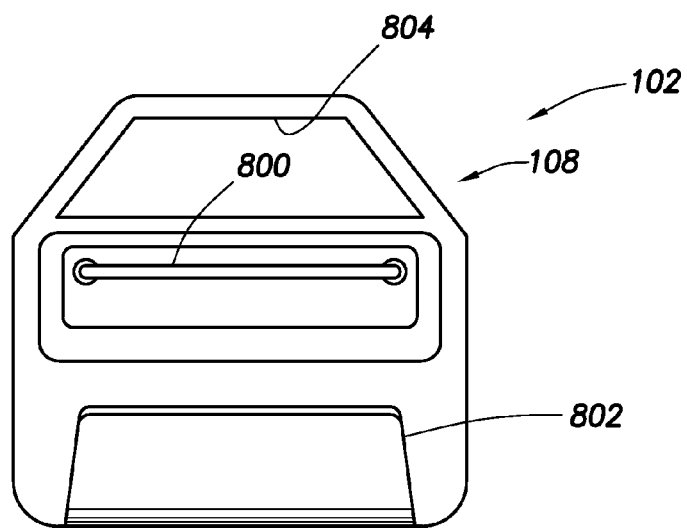
FIG. 8 shows a front elevation view of a wand in accordance with at least some embodiments.

The various embodiments discussed to this point have had two active electrodes. However, other numbers of active electrodes may be equivalently used. For example, FIG. 8 shows an end elevation view of the distal end 108 of wand 102 comprising a single active electrode 800, and correspondingly the width of the discharge aperture (not visible) the conductive plate 802 and aperture 804 are smaller as well. Likewise, FIG. 9 shows an end elevation view of the distal end 108 of wand 102 comprising an illustrative three active electrodes 900, 902 and 904, and correspondingly the width of the discharge aperture 906 (illustratively visible in these embodiments) the conductive plate 908 and aperture 910 are larger as well. One may use the wand 102 having a distal end 108 as shown in FIG. 8 as the situation dictates, for example for smaller wounds or wounds in hard to reach locations. Likewise, one may use the wand 102 having a distal end 108 as shown in FIG. 9 as the situation dictates, for example larger wounds and/or areas easier to reach.

Figure 10:
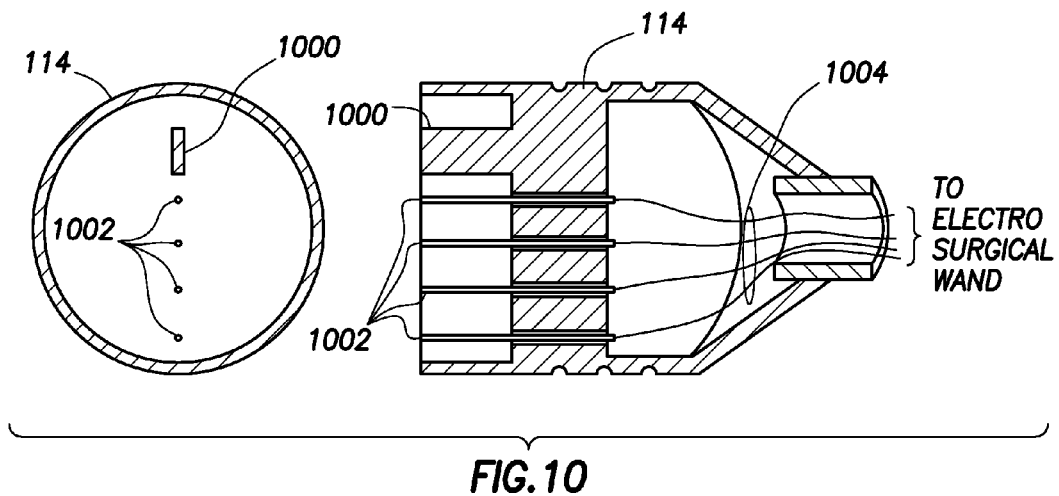
FIG. 10 shows both an elevation end-view (left) and a cross-sectional view (right) of a wand connector in accordance with at least some embodiments.

As illustrated in FIG. 1, flexible multi-conductor cable 112 (and more particularly its constituent electrical leads) couple to the wand connector 114. Wand connector 114 couples the controller 104, and more particularly the controller connector 120. FIG. 10 shows both a cross-sectional view (right) and an end elevation view (left) of wand connector 114 in accordance with at least some embodiments. In particular, wand connector 114 comprises a tab 1000. Tab 1000 works in conjunction with a slot on controller connector 120 (shown in FIG. 11) to ensure that the wand connector 114 and controller connector 120 only couple in one relative orientation. The illustrative wand connector 114 further comprises a plurality of electrical pins 1002 protruding from wand connector 114. In many cases, the electrical pins 1002 are coupled one each to an electrical lead of electrical leads 1004, which leads are electrically coupled to active and return electrodes. Stated otherwise, in a particular embodiment each electrical pin 1002 couples to a single electrical lead, and thus each illustrative electrical pin 1002 couples to a single electrode of the wand 102. In other cases, a single electrical pin 1002 couples to multiple electrodes (e.g., multiple active electrodes, or multiple return electrodes) on the electrosurgical wand 102. While FIG. 10 shows four illustrative electrical pins, in some embodiments as few as two electrical pins, and as many as 26 electrical pins, may be present in the wand connector 114.

Figure 11:
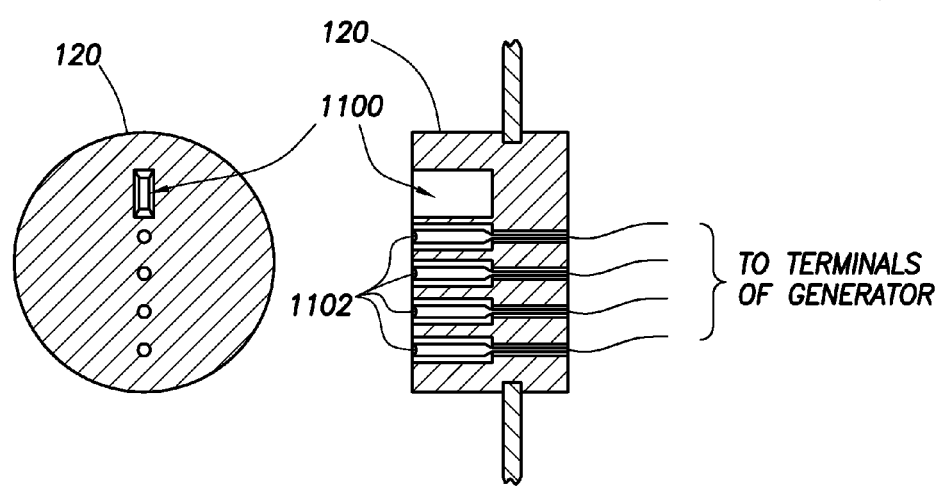
FIG. 11 shows both an elevation end-view (left) and a cross-sectional view (right) of a controller connector in accordance with at least some embodiments.

FIG. 11 shows both a cross-sectional view (right) and an end elevation view (left) of controller connector 120 in accordance with at least some embodiments. In particular, controller connector 120 comprises a slot 1100. Slot 1100 works in conjunction with a tab 1000 on wand connector 114 (shown in FIG. 10) to ensure that the wand connector 114 and controller connector 120 only couple in one orientation. The illustrative controller connector 120 further comprises a plurality of electrical pins 1102 residing within respective holes of controller connector 120. The electrical pins 1102 are coupled to terminals of a voltage generator within the controller 104 (discussed more thoroughly below). When wand connector 114 and controller connector 120 are coupled, each electrical pin 1102 couples to a single electrical pin 1002. While FIG. 11 shows only four illustrative electrical pins, in some embodiments as few as two electrical pins and as many as 26 electrical pins may be present in the wand connector 120.

While illustrative wand connector 114 is shown to have the tab 1000 and male electrical pins 1002, and controller connector 120 is shown to have the slot 1100 and female electrical pins 1102, in alternative embodiments the wand connector has the female electrical pins and slot, and the controller connector 120 has the tab and male electrical pins, or other combination. In other embodiments, the arrangement of the pins within the connectors may enable only a single orientation for connection of the connectors, and thus the tab and slot arrangement may be omitted. In yet still other embodiments, other mechanical arrangements to ensure the wand connector and controller connector couple in only one orientation may be equivalently used.

FIG. 12 illustrates a controller 104 in accordance with at least some embodiments. In particular, FIG. 12 illustrates the controller 104 coupled to the wand 102, where the wand 102 is shown in simplified form comprising the active electrodes 202/204, the conductive plate 210 acting as a return electrode 210, and electrical leads coupled to the controller 104. The controller 104 comprises a processor 1200. The processor 1200 may be a microcontroller, and therefore the microcontroller may be integral with random access memory (RAM) 1202, read-only memory (ROM) 1204, digital-to-analog converter (D/A) 1206, digital outputs (D/O) 1208 and digital inputs (D/I) 1210. The processor 1200 may further provide one or more externally available peripheral busses, such as a serial bus (e.g., I$^2$C), parallel bus, or other bus and corresponding communication mode. The processor 1200 may further be integral with a communication logic 1212 to enable the processor 1200 to communicate with external devices, as well as internal devices, such as display device 124. Although in some embodiments the controller 104 may implement a microcontroller, in yet other embodiments the processor 1200 may be implemented as a standalone central processing unit in combination with individual RAM, ROM, communication, D/A, D/O and D/I devices, as well as communication port hardware for communication to peripheral components.

ROM 1204 stores instructions executable by the processor 1200. In particular, the ROM 1204 may comprise a software program that implements the various embodiments of controlling the voltage generator 1216 (responsive to commands from the user), as well as interfacing with the user by way of the display device 124 and/or the foot pedal assembly 130 (FIG. 1). The RAM 1202 may be the working memory for the processor 1200, where data may be temporarily stored and from which instructions may be executed. Processor 1200 couples to other devices within the controller 104 by way of the D/A converter 1206 (e.g., the voltage generator 1216), digital outputs 808 (e.g., the voltage generator 1216), digital inputs 1210 (i.e., push button switches 126, and the foot pedal assembly 130 (FIG. 1)), and other peripheral devices.

Voltage generator 1216 generates selectable alternating current (AC) voltages that are applied to the electrodes of the wand 102. In various embodiments, the voltage generator defines two terminals 1224 and 1226. The terminals 1224 and 1226 may couple to active electrodes and return electrodes. As an example, terminal 1224 couples to illustrative active electrodes 202 and 204, and terminal 1226 couples to the conductive plate 210 acting as return electrode. In accordance with the various embodiments, the voltage generator generates an alternating current (AC) voltage across the terminals 1224 and 1226. In at least some embodiments the voltage generator 1216 is electrically "floated" from the balance of the supply power in the controller 104, and thus the voltage on terminals 1224, 1226, when measured with respect to the earth ground or common (e.g., common 1228) within the controller 104, may or may not show a voltage difference even when the voltage generator 1216 is active.

The voltage generated and applied between the active terminal 1224 and return terminal 1226 by the voltage generator 1216 is a RF signal that, in some embodiments, has a frequency of between about 5 kilo-Hertz (kHz) and 20 Mega-Hertz (MHz), in some cases being between about 30 kHz and 2.5 MHz, often between about 100 kHz and 200 kHz. The RMS (root mean square) voltage generated by the voltage generator 816 may be in the range from about 5 Volts (V) to 1000 V, preferably being in the range from about 10 V to 500 V, often between about 100 V to 350 V depending on the active electrode size and the operating frequency. The peak-to-peak voltage generated by the voltage generator 1216 for ablation for wound treatment in some embodiments is a square wave form in the range of 10 V to 2000 V and in some cases in the range of 100 V to 1800 V and in other cases in the range of about 28 V to 1200 V, often in the range of about 100 V to 320V peak-to-peak (again, depending on the electrode size and the operating frequency).

Still referring to the voltage generator 1216, the voltage generator 1216 delivers average energy levels ranging from several milliwatts to hundreds of watts per electrode, depending on the voltage applied for the target tissue being treated, and/or the maximum allowed temperature selected for the wand 102. The voltage generator 1216 is configured to enable a user to select the voltage level according to the specific requirements of a particular procedure. A description of one suitable voltage generator 1216 can be found in commonly assigned U.S. Pat. Nos. 6,142,992 and 6,235,020, the complete disclosure of both patents are incorporated herein by reference for all purposes.

In some embodiments, the various operational modes of the voltage generator 1216 may be controlled by way of digital-to-analog converter 1206. That is, for example, the processor 1200 may control the output voltage by providing a variable voltage to the voltage generator 1216, where the voltage provided is proportional to the voltage generated by the voltage generator 1216. In other embodiments, the processor 1200 may communicate with the voltage generator by way of one or more digital output signals from the digital output 1208 device, or by way of packet based communications using the communication device 1212 (connection not specifically shown so as not to unduly complicate FIG. 12).

FIG. 13 shows a method in accordance with at least some embodiments. In particular, the method starts (block 1300) and comprises: flowing a conductive fluid within a fluid conduit disposed within a electrosurgical wand, the conductive fluid is discharged through a discharge aperture in the direction of a return electrode, and the return electrode directs at least a portion of the conductive fluid toward an active electrode (block 1302); applying electrical energy between the active and return electrodes (block 1304); forming, responsive to the energy, a plasma proximate to the active electrode (block 1306); and treating a wound by placing the active electrode against the wound, and translating the active electrode along the wound (block 1308). Thereafter the method ends (block 1310).

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical wand comprising:
   an elongate housing that defines a handle end and a distal end;
   a connector comprising a first and second electrical pins;
   an aspiration aperture on the distal end of the elongate housing, the aspiration aperture fluidly coupled to a first fluid conduit, the first fluid conduit within the elongate housing;
   a discharge aperture on the distal end of the elongate housing, the discharge aperture fluidly coupled to a second fluid conduit, and the second fluid conduit within the elongate housing;
   a first active electrode of conductive material on the distal end of the elongate housing, the first active electrode between the discharge aperture and the aspiration aperture, and the first active electrode electrically coupled to the first electrical pin; and
   a conductive plate that abuts the discharge aperture, at least a portion of the conductive plate disposed over the discharge aperture, and the conductive plate electrically coupled to the second electrical pin.

2. The electrosurgical wand of claim 1 wherein the conductive plate defines a lip portion, and wherein at least a portion of the lip portion is disposed over the discharge aperture.

3. The electrosurgical wand of claim 2 wherein the lip portion is defined between a distal end of the conductive plate and a bend in the conductive plate.

4. The electrosurgical wand of claim 2 wherein the conductive plate has a curved portion and the lip portion is the distal end of the conductive plate.

5. The electrosurgical wand of claim 1 further comprising:
   the first active electrode defines a first exposed surface area; and
   the conductive plate defines a second exposed surface area greater than the first exposed surface area.

6. The electrosurgical wand of claim 1 wherein when viewed perpendicularly to a plane defined by the discharge aperture, the conductive plate occludes more than half an area defined by the discharge aperture.

7. The electrosurgical wand of claim 1 wherein first active electrode further comprises a loop of wire that defines a straight portion and two standoff portions.

8. The electrosurgical wand of claim 7 wherein the first active electrode has a standoff distance between and including 0.010 and 0.050 inches.

9. The electrosurgical wand of claim 7 wherein the first active electrode has a standoff distance of between and including 0.015 and 0.025 inches.

10. The electrosurgical wand of claim 7 wherein the loop of wire has a diameter of between and including 0.008 and 0.015 inches.

11. The electrosurgical wand of claim 7 wherein the loop of wire has a diameter of 0.010 inches.

12. The electrosurgical wand of claim 1 wherein at least a portion of the aspiration aperture is closer to the handle than the any portion of the discharge aperture.

13. The electrosurgical wand of claim 1 further comprising:
   the distal end of the elongate housing defines a width and a thickness;
   wherein first active electrode further comprises a loop of wire that defines a first straight portion;
   a second active electrode that comprises a loop of wire that defines a second straight portion; and
   the first and second straight portions are aligned along the width such that, when viewed along the thickness, the first and second straight portions overlap.

14. The electrosurgical wand of claim 13 wherein the first straight portion and the second straight portion are parallel.

15. The electrosurgical wand of claim 1 wherein the aspiration aperture defines an aperture width, and wherein the second fluid conduit transitions in width from the aperture width to an internal width over a length not less than two times the difference between the aperture width and the internal width.

16. A system comprising:
   an electrosurgical controller, the electrosurgical controller configured to produce radio frequency (RF) energy at an active terminal with respect to a return terminal;

an electrosurgical wand coupled to the electrosurgical controller, the electrosurgical wand comprising:
an elongate housing that defines a handle end and a distal end;
an aspiration aperture on the distal end of the elongate housing, the aspiration aperture fluidly coupled to a first fluid conduit, the first fluid conduit within the elongate housing;
a discharge aperture on the distal end of the elongate housing, the discharge aperture fluidly coupled to a second fluid conduit, and the second fluid conduit within the elongate housing;
a first active electrode of conductive material on the distal end of the elongate housing, the first active electrode between the discharge aperture and the aspiration aperture, and the first active electrode electrically coupled to active terminal of the electrosurgical controller; and
a conductive plate that abuts the discharge aperture, at least a portion of the conductive plate disposed over the discharge aperture, and the conductive plate electrically coupled to the return terminal of the electrosurgical controller.

17. The electrosurgical wand of claim 16 wherein the conductive plate defines a plane, and wherein an angle between the plane and the discharge aperture is an acute angle.

18. The electrosurgical wand of claim 16 wherein the conductive plate defines a straight portion and a lip portion, and wherein at least a portion of the lip portion is disposed over the discharge aperture.

19. The electrosurgical wand of claim 18 wherein the lip portion is defined between a distal end of the conductive plate and a bend in a medial portion of the conductive plate.

20. The electrosurgical wand of claim 18 wherein the conductive plate has a curved portion and the lip portion is the distal end of the conductive plate.

21. The electrosurgical wand of claim 16 further comprising:
the first active electrode defines a first exposed surface area; and
the conductive plate defines a second exposed surface area greater than the first exposed surface area.

22. The electrosurgical wand of claim 16 wherein when viewed perpendicularly to a plane defined by the discharge aperture, the return electrode occludes more than half an area defined by the discharge aperture.

23. The electrosurgical wand of claim 16 wherein first active electrode further comprises a loop of wire that defines a straight portion and two standoff portions.

24. The electrosurgical wand of claim 16 wherein at least a portion of the aspiration aperture is closer to the handle than the any portion of the discharge aperture.

25. The electrosurgical wand of claim 16 further comprising:
the distal end of the elongate housing defines a width and a thickness;
wherein first active electrode further comprises a loop of wire that defines a first straight portion;
a second active electrode that comprises a loop of wire that defines a second straight portion; and
the first and second straight portions are aligned along the width such that, when viewed along the thickness, the first and second straight portions overlap.

26. The electrosurgical wand of claim 25 wherein the first straight portion and the second straight portion are parallel.

* * * * *